United States Patent
Czernicki

(10) Patent No.: US 7,232,416 B2
(45) Date of Patent: Jun. 19, 2007

(54) METHOD AND DEVICE FOR DETERMINING THE ANATOMICAL CONDITION OF A HUMAN BEING OR AN ANIMAL AND A STRENGTH TRAINING MACHINE AND A COMPUTER PROGRAM WHICH IS SAVED TO A MEMORY MEDIUM

(76) Inventor: Jacek Czernicki, Sachsenkamstr 28 A, Munich (DE) 81369

( * ) Notice: Subject to any disclaimer, the term of this patent is extended or adjusted under 35 U.S.C. 154(b) by 339 days.

(21) Appl. No.: 10/258,357

(22) PCT Filed: Apr. 12, 2001

(86) PCT No.: PCT/EP01/04240

§ 371 (c)(1),
(2), (4) Date: Apr. 23, 2003

(87) PCT Pub. No.: WO01/78645

PCT Pub. Date: Oct. 25, 2001

(65) Prior Publication Data

US 2004/0054302 A1    Mar. 18, 2004

(51) Int. Cl.
*A61B 5/103* (2006.01)
*A61B 5/117* (2006.01)
*A61B 5/00* (2006.01)
*A61B 7/00* (2006.01)
*A61M 25/00* (2006.01)
*A63B 21/005* (2006.01)
*A63B 71/00* (2006.01)

(52) U.S. Cl. .................. 600/595; 600/585; 600/586; 600/587; 482/6; 482/8

(58) Field of Classification Search ............ 600/586, 600/587, 595, 585; 601/33, 23; 482/6, 8
See application file for complete search history.

(56) References Cited

U.S. PATENT DOCUMENTS 3,181,528 A * 5/1965 Brackin .................. 600/586

(Continued)

FOREIGN PATENT DOCUMENTS

AT        388 864 B        9/1989

(Continued)

OTHER PUBLICATIONS

S. Tavathia et al., "Analysis of Knee Vibration Signals Using Linear Prediction", *IEEE Transactions on Biomedical Engineering*, vol. 39, No. 9, pp. 959-970, Sep. 1992.

(Continued)

*Primary Examiner*—Max F. Hindenburg
*Assistant Examiner*—Jeffrey G. Hoekstra
(74) *Attorney, Agent, or Firm*—Sierra Patent Group, Ltd.

(57) ABSTRACT

A method for determining the anatomic condition of components of the body of a human or of an animal is disclosed comprising producing a sound signal in a selected component of the body by at least one of passive and active movements of at least one joint. The method includes recording a sound signal at a point adjacent to the selected component of the body and evaluating the sound signal. An auxiliary device selected from the group consisting of a splint, an orthosis and an exercise machine is used which ensures a repeatable movement determined by the design of the auxiliary device. The sound signal caused by the movement is recorded and evaluated by a spectral analysis of frequencies and amplitudes contained in the sound signal. A comparison is made with reference patterns of the spectral analyses for the diagnosis of the anatomic condition. The result of a diagnosis is indicated as at least one of a print out and a screen display and wherein the joint investigated is schematically illustrated on the screen display, optionally with associated soft tissues, tendons and ligaments. The diagnosis is indicated visually, by at least one of coloring, lighting up of and flashing of damaged positions.

6 Claims, 11 Drawing Sheets

U.S. PATENT DOCUMENTS

| | | | | |
|---|---|---|---|---|
| 3,847,141 A | | 11/1974 | Hoop | 128/2 V |
| 4,437,473 A | | 3/1984 | Mollan | 128/773 |
| 4,823,807 A | * | 4/1989 | Russell et al. | 600/586 |
| 4,836,218 A | | 6/1989 | Gay et al. | 128/773 |
| 4,905,671 A | | 3/1990 | Senge et al. | 128/24 A |
| 4,905,676 A | * | 3/1990 | Bond et al. | 601/34 |
| 4,982,328 A | * | 1/1991 | Kasugai | 600/410 |
| 4,991,581 A | * | 2/1991 | Andries | 600/528 |
| 5,099,859 A | * | 3/1992 | Bell | 600/594 |
| 5,213,555 A | | 5/1993 | Hood et al. | 482/57 |
| 5,368,044 A | | 11/1994 | Cain et al. | 128/739 |
| 5,396,891 A | | 3/1995 | Whitney et al. | 128/661.03 |
| 5,402,781 A | | 4/1995 | Dimarogonas | 128/653.1 |
| 5,413,116 A | * | 5/1995 | Radke et al. | 600/590 |
| 5,800,363 A | | 9/1998 | Cheng et al. | 600/587 |
| 5,806,520 A | | 9/1998 | Berger et al. | 128/660.06 |
| 5,836,876 A | | 11/1998 | Dimarogonas | 600/407 |
| 5,897,510 A | | 4/1999 | Keller et al. | 600/594 |
| 5,931,763 A | | 8/1999 | Alessandri | 482/4 |
| 6,015,383 A | | 1/2000 | Buhler et al. | 600/437 |
| 6,024,711 A | | 2/2000 | Lentle et al. | 600/586 |
| 6,135,960 A | | 10/2000 | Holberg | 600/447 |
| 6,162,189 A | * | 12/2000 | Girone et al. | 600/592 |

FOREIGN PATENT DOCUMENTS

| | | |
|---|---|---|
| DE | 40 30 488 A1 | 4/1991 |
| DE | 44 05 454 A1 | 8/1995 |
| DE | 196 35 957 A1 | 3/1998 |
| DE | 197 14 899 A1 | 10/1998 |
| GB | 2 156 983 A | 10/1985 |
| WO | WO 01/078645 A3 | 10/2001 |

OTHER PUBLICATIONS

E. Bukhman et al., "Spectral Analysis of Acoustic Vibrations on the Surface fo the Human Body", *Acoustical Physics*, vol. 41, No. 1, pp. 41-48, Jan./Feb. 1995.

\* cited by examiner

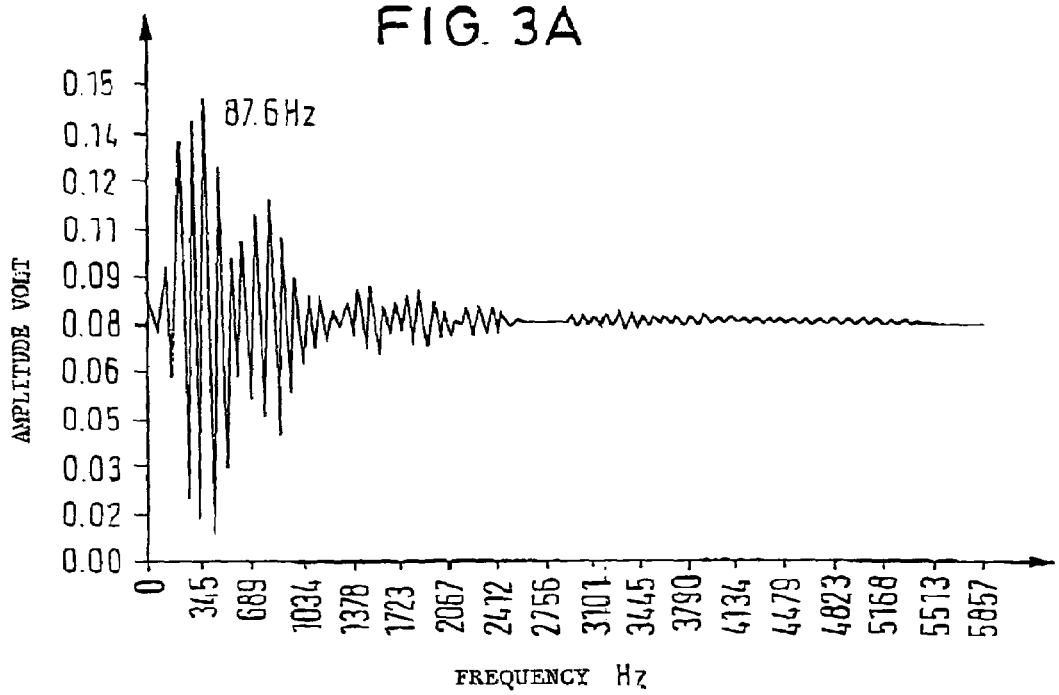
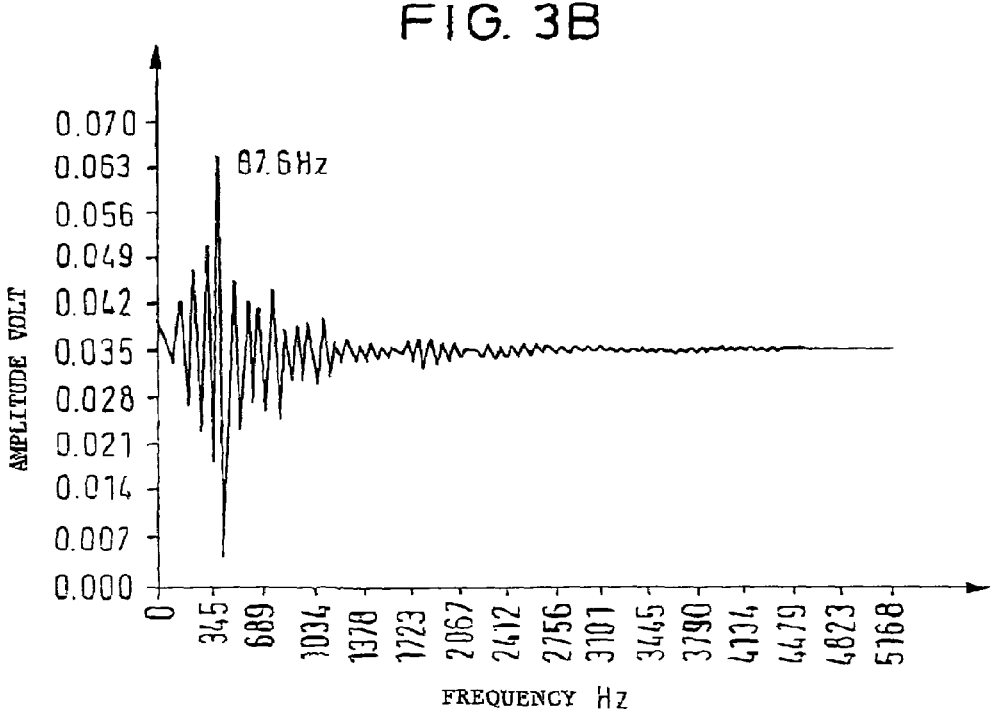

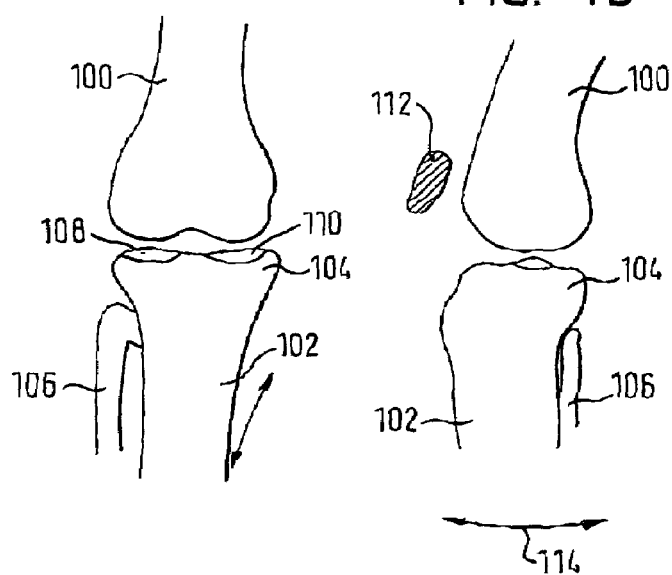
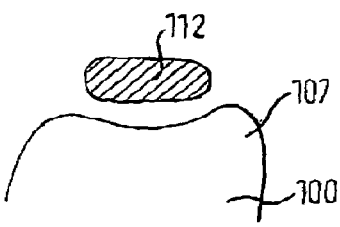
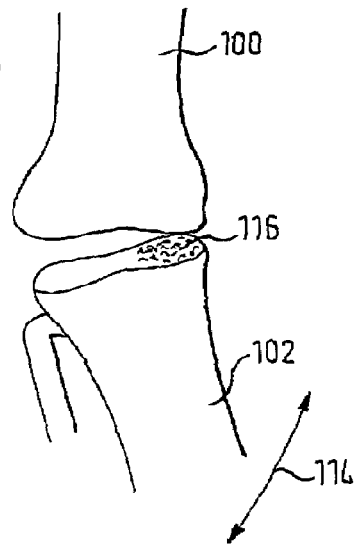

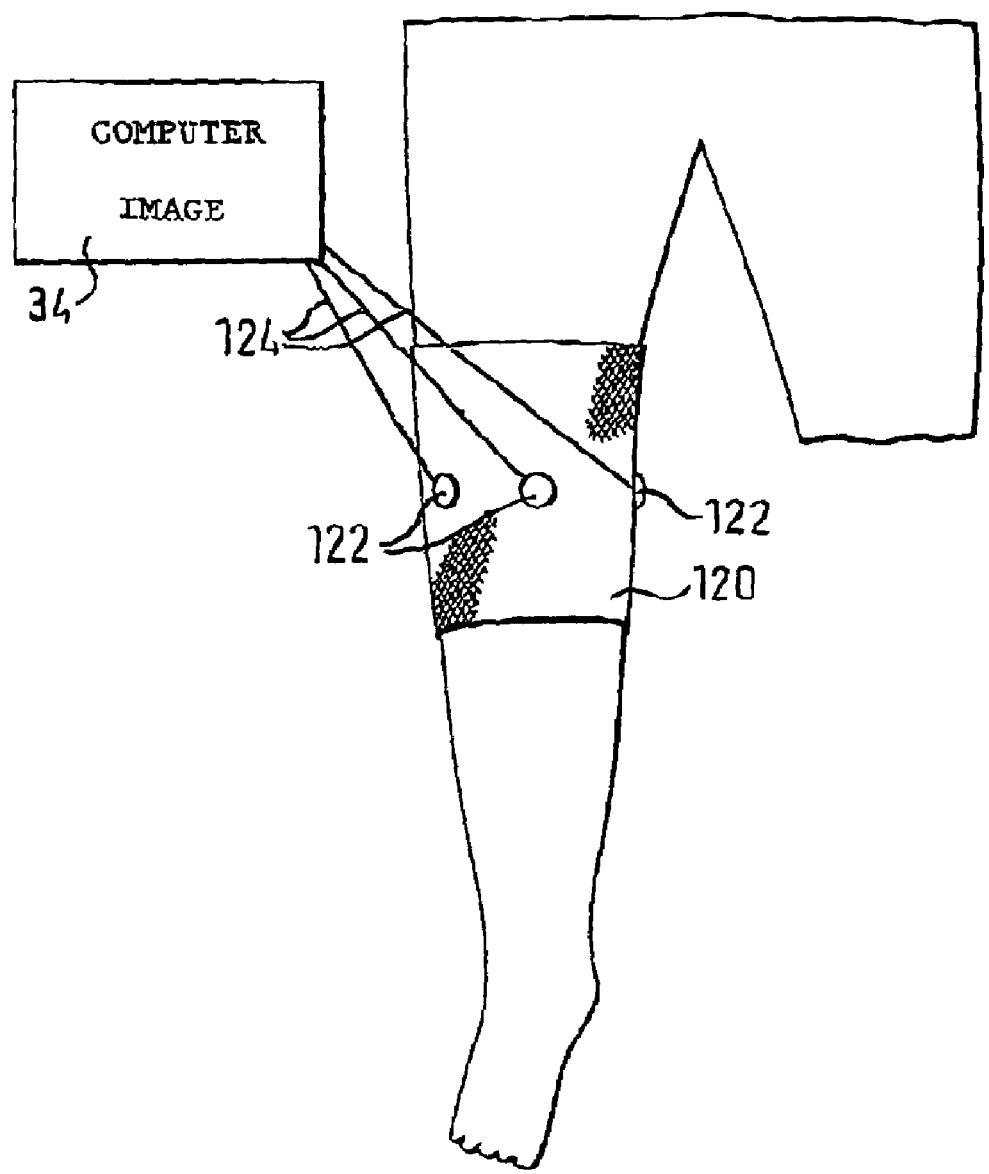

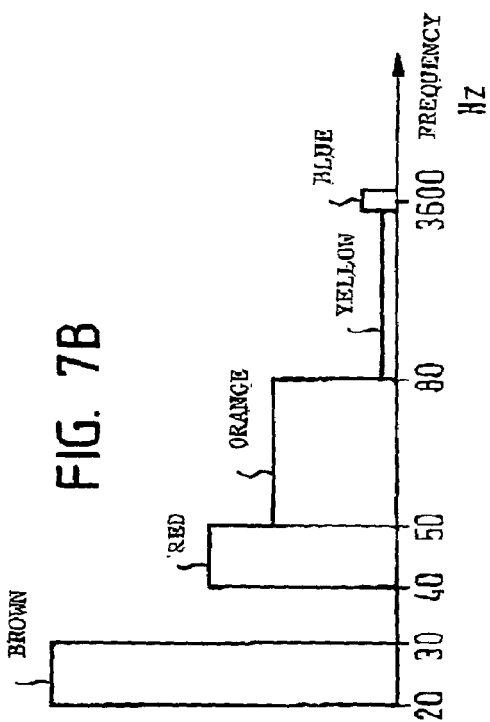
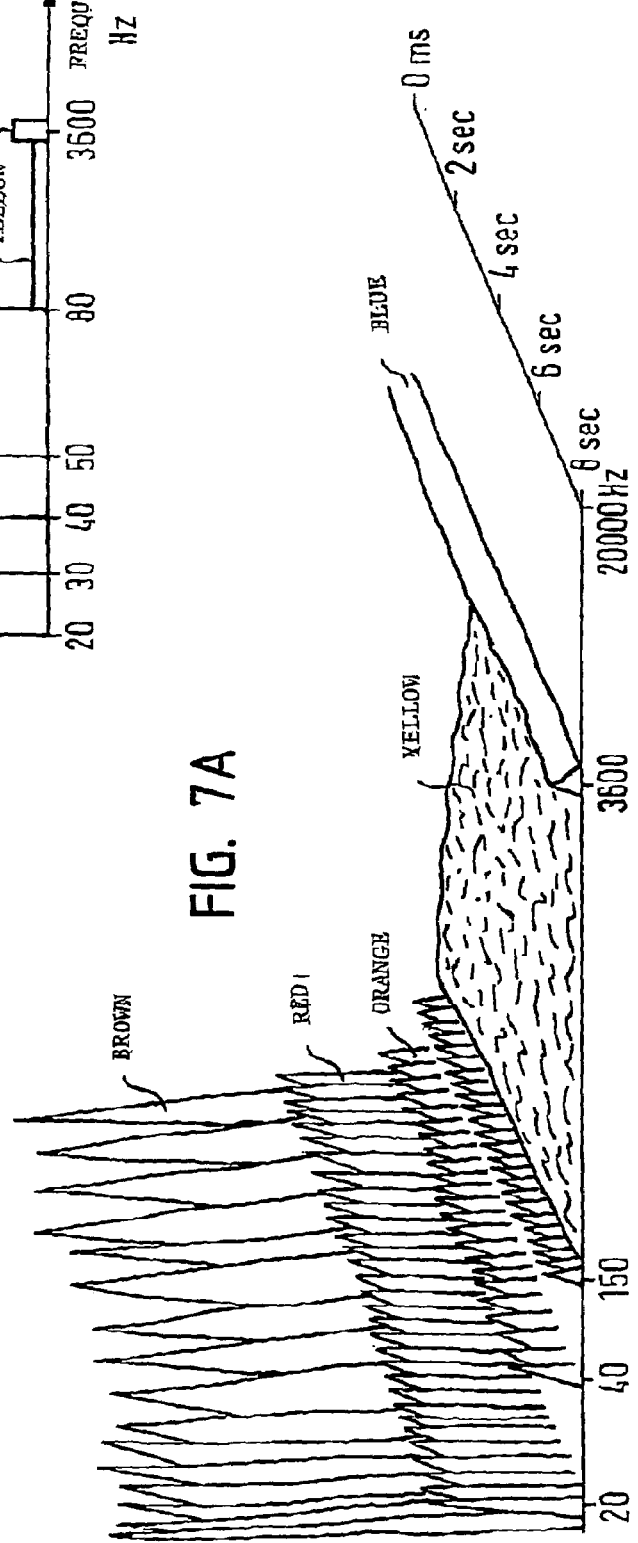
FIG. 7B
FIG. 7A

METHOD AND DEVICE FOR DETERMINING THE ANATOMICAL CONDITION OF A HUMAN BEING OR AN ANIMAL AND A STRENGTH TRAINING MACHINE AND A COMPUTER PROGRAM WHICH IS SAVED TO A MEMORY MEDIUM

BACKGROUND

The present invention relates to a method and to an apparatus for determining the anatomic condition of components of the body of a human or of an animal and also to an exercise machine, in particular an adjustable exercise machine and to a computer program stored on a storage medium.

Although the present invention is principally concerned with diseases of the joints and soft tissues, or their therapeutic treatment and rehabilitation and also with corresponding apparatuses, the term "osteoporosis" and the significance of the illness should be briefly explained in order to be better able to explain the invention.

In accordance with various sources there are in Germany about 6–8 million people suffering from osteoporosis. As a result of the ¼ million fractures, in particular fractures of the neck of the femur, the cost of treating osteoporosis and the consequence of osteoporosis reach a sum in the tens of billions.

The bone substance undergoes a physiological restructuring. The cells which build up the bone mass and for example repair it after fracture are osteoblasts. They take calcium and other minerals from the blood and bind it in the bones. In this manner the bone substance becomes stronger. The other type of cells which break down bone substance and prevent excess bone growth are named osteoclasts.

In the physiological condition equilibrium exists between the two processes. With increasing age the decomposition of bones takes the upper hand. Some sources state that from the $25^{th}$ year of life onwards there is an increased break down of the bones, both in men and also in women.

Stated simply one understands under the term osteoporosis a porous fragile bone. Medically one has to distinguish it however from a relatively rare illness, osteomalacia. Both osteoporosis and also osteomalacia fall medically beneath the generic term osteopenie.

Independently of the causes of osteoporosis in women and men the same picture generating measures are used. The bone density is most frequently investigated by means of computer tomography. This method has however many disadvantages, such as exposure to radiation and influencing of the measurement results in the lower LWS by changes such as spondylophytes, osteochondrosis etc.

The increasingly most frequent method is the measurement with ultra sound. The patients are however here forced into orthopaedic and gynaecological practices in order to undergo an ultrasonic investigation. The precision of this measurement is, however, hitherto very unreliable as is known from the literature and from daily practice. The bone densitometry by means of ultra sound takes place in a frequency range from 200 kHz to 1 MHz and is additionally restricted by the legally prescribed health insurers. This is done for two reasons: on the one hand, as a result of the relatively high costs amounting to an average of 80–130 DM per investigation and, on the other hand, as a result of the above discussed unreliability of this method.

X-ray diagnosis only reliably shows osteoporotic changes when the reduction in bone density has passed about 30 percent. Densitometrie is in such cases no longer useful. Appropriate treatment is commenced even without this investigation.

The object of the invention is to set forth a new method and a new apparatus with which one can reliably carry out a series of investigations and diagnoses in connection with the anatomic condition of components of the body of an human or of an animal at favourable cost and indeed without having to carry out medical surgery or to take samples.

SUMMARY

In order to satisfy this object the method of the invention is characterized in that one produces a sound signal in the selected component by passive or active movements of at least one joint and records a sound signal at a point adjacent to the component and evaluates it.

An apparatus for carrying out the method of the invention consists of a sound recording device, a device which carries out a signal analysis and which preferably includes a low pass filter or a low pass function, and an output device for outputting the results of the signal analysis.

The invention is based on the recognition that sound signals, which are caused by movement of a joint in components of the body of an human or of an animal, enable, on appropriate evaluation, conclusions to be drawn on the condition of the respective components. For example the evaluation allows statements to be made concerning the material characteristics, the degree of mineralization, the ultra structure, the collagen structure, the micro structure and the geometry of the bone. Above all, however, the evaluation allows statements to be made concerning the anatomic condition of joints and of the soft tissues associated with them.

The evaluation can take place in accordance with the invention by filtration and spectral analysis and also includes in many cases a comparison with the reference values or reference patterns. In this connection the filtering that is used is normally understood as low pass filtering, for example in the range up to about 10 kHz. In this way the bandwidth is restricted. The analysis and evaluation is advantageously carried out by means of a computer program.

Under active movements one understands that the patient himself moves a selected joint. In contrast, for passive movements, a device is used which forces the movement of a selected joint. Advantageous in the use of active movements is that the patient is not made insecure or anxious by technical apparatus.

On the other hand, with passive movements, the speed and amplitude of the movement can be precisely and repeatedly preset so that the results from different patients can be better compared to one another here.

A special case of the passive generation of movement lies in the situation in which the doctor or another person moves the joint manually.

The invention is however not restricted to this. Examples for further possible applications are:
1. Checking the bone consolidation (callus formation following fractures). With conservative therapy, i.e., without operational treatment, this measure can certainly be used. For osteosynthetically treated bone fractures certain problems result with reliable references as a result of the diversity of the methods and the different types of metal implants.
   Advantage: X-ray checks can be reduced to a minimum with conservatively treated fractures.

2. Signal analysis of both legs with diffuse complaints, for example lower legs with young patients. It is known that primary bone lesions (tumours) statistically arise frequently in this group of patients.

An advantage lies in the fact that the measurement result can be used as an aid to a decision, as to whether further investigations are appropriate. For example, the absence of a difference between the two lower extremities can count as a reason for dispensing with further image forming processes.

When a difference of the signal analyses is present further investigations such as X-ray investigations or scintigraphic imaging must be carried out.

3. For many other bone diseases, for example plasmozytoma (malignant tumour) the scull is frequently afflicted ("moth holes"). The tapping and signal analysis of the skull can preclude or confirm plastic and lytic bone changes. The consequences are further investigations such as X-ray investigations or computer tomography.

4. The above named method can be used above all with diseases of the joints and soft tissue lesions. These include arthrosis (cartilage loss). Every person is effected by this in the course of life. The possibility of attaching a plurality of sensors at different positions is of advantage. In this way osteoarthroses of the knee (wear of the knee joint) can be precisely differentiated. It is assumed that a determination can be made on the basis of the signal analysis whether this is wear of the inner joint gap or of the outer joint gap. Wear of the rear of the patella could also be diagnosed.

With respect to the patella (knee cap) there are always diagnostic problems and indeed both clinical and also with image giving methods such as NMR. By means of the signal analysis carried out in accordance with the invention it can be determined whether problems are present at all at the rear side of the patella. The corresponding noises (spectra) can be associated with specific diseases from chondropathic patella, chondromalacic patella to retropatella arthrosis (cartilage loss at the rear side of the patella or of the sliding support for the patella).

5. The method can also be used for various soft tissue diseases, for example:
pathology of the meniscus,
extent of achillodynia (the grating of the "paratenon") in addition to sono-graphic estimation of the pathological situation.
coxa saltans (snapping hips).
labrum lesion of the shoulder joints.
rotator cuff lesions of the shoulder for example narrowing (M. supraspinatus)
discus triangularis lesion—hitherto the biggest diagnostic problem even by means of NMR of the hand joint.

Possibly, one can obtain additional diagnostic advantages through the signal analysis carried out in accordance with the invention.

6. A further conceivable application would be the portrayal of the carpal tunnel syndrome (very frequent disease—narrowing of the N. medianus in the carpal tunnel of the hand joint). This illness causes thousands of operations per year in Germany.

The diagnosis is normally made by means of nerve speed measurements of the N. medianus. Theoretically diagnosis appears to be possible with analysis of, for example, the tapping sound of the carpal tunnel (the tapping of the carpal tunnel is termed Hoffmann-Tinel-Test in orthopedics. In this test the result of the tapping is however not evaluated acoustically but rather through the subjective sense of pain of the patient). Appropriate references can possibly be found here.

BRIEF DESCRIPTION OF THE DRAWINGS

The invention will be explained in more detail with reference to embodiments and to the accompanying drawings in which FIGS. 4 to 10 show examples of the invention. There are shown:

FIG. 1 a schematic diagram for the explanation of the method of the invention,

FIG. 2 a schematic diagram for the explanation of a possible variant of the signal evaluation in the method of FIG. 1, FIG. 3A the result of a measurement in accordance with the invention on a healthy male patient of 42 years of age, FIG. 3B the result of a measurement in accordance with the invention of a male patient suffering from osteoporosis and aged 44, FIG. 3C the result of a measurement in accordance with the invention on a female patient suffering from osteoporosis and aged 64, FIG. 3D the result of a measurement in accordance with the invention on an older female patient suffering from pronounced osteoporosis and aged 72, FIG. 3E the recorded sound signal from the same patient as considered in FIG. 3A and FIG. 3F the recorded sound signal from the same patient as considered in FIG. 3C, FIGS. 4A to 4C schematic representations of a healthy human knee joint, FIG. 4D a schematic illustration of a human knee joint suffering under medial osteoarthrosis, FIG. 5 a schematic illustration of a sound recording device in accordance with the invention, FIG. 6A an orthosis for the knee joint, FIG. 6B a modification of the orthosis of FIG. 6A in accordance with the invention, FIG. 7A a spectral analysis of sound signals of a healthy human knee joint in accordance with the FIGS. 4A to 4C, FIG. 7B a histogram corresponding to FIG. 7A, FIG. 8A a spectral analysis of sound signals of a human knee joint in accordance with FIG. 4D suffering medial osteoarthrosis, FIG. 8B a histogram corresponding to FIG. 8A, FIG. 9A a schematic representation of an exercise machine usable for the invention, FIG. 9B a schematic diagram to explain an inventive setting of an exercise machine in accordance with FIG. 9A and FIG. 10 a schematic representation of an apparatus with animation in accordance with the invention.

DETAILED DESCRIPTION

Noises arise in the human body through movements and internal friction. These noises can say something concerning the inner condition of the body. In the description attention is particularly directed to bone and joint noises. First of all a principle methodology for the determination and evaluation of these noises will be described, which has been investigated in the practice of the applicant in the diagnosis of osteoporosis. Then—building on this description—the present invention will be further explained with reference to FIGS. 4 to 10. In diagnosing osteoporosis one is concerned primarily with the evaluation of the tapping noises (longitudinal vibrations) which are initiated with a device which always delivers the same pulses. One taps the selected measurement position (tibia head anatomically hardly any soft tissue cover) about 5 cm caudal.

Noises are basically longitudinal air vibrations which can be perceived by our ears. After reception they can be analyzed by the brain into a very broad spectrum. The human brain is able to recognize certain patterns from a sound—pattern recognition—or to sort out specific tones from it (filtering).

All these abilities are in reality very complicated mechanisms which first become aware to us on attempting to realize these abilities artificially.

Precisely these problems have occupied scientists from all fields for decades. In the course of the years ever more powerful tools (systems) have arisen for the analysis or pattern recognition of sound signals. One can see this in the performance of modern speech recognition programs which have improved dramatically.

Before the discussion of the analysis of the signal starts the obtaining of the signals and the correct preparation of the signals should be described.

The sounds which are of interest to us can arise in two ways.

The one possibility is through movement. If one moves a joint in a specific direction, this leads to an internal friction in the joint which one can hear.

The second possibility assumes there is an outer impact on the bone which brings it to oscillation which can again be listened to.

In addition reference should be made to noises of the soft tissues, for example the musculature in the shoulder region, the special anatomic structure in the hand joint, etc. Such noises can likewise be evaluated in accordance with the invention and lead to improve diagnoses of the corresponding components.

Figure 1:
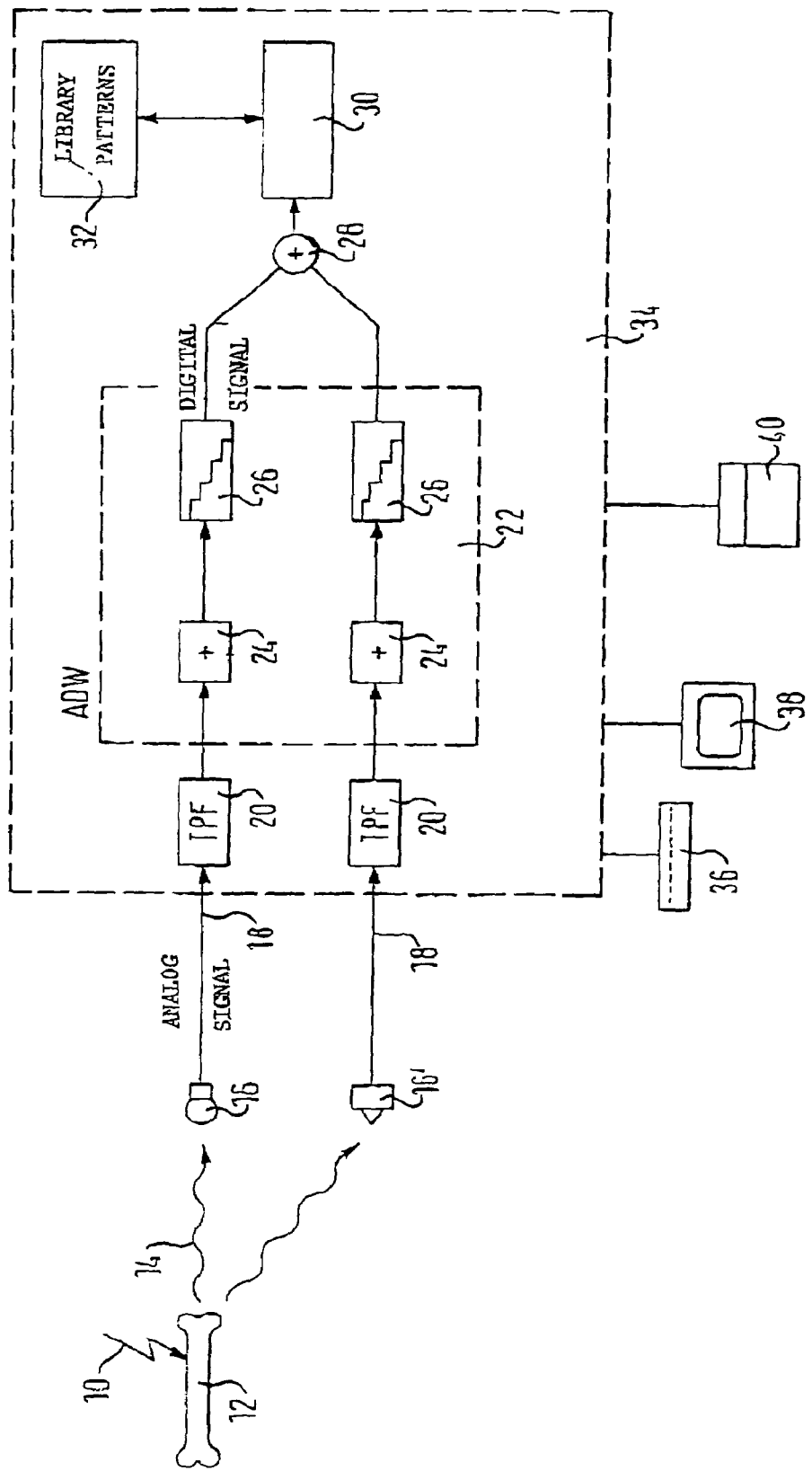
FIGS. 1 to 3 show a method for the diagnosis of osteoporosis whereas the further

The processing of the sounds in accordance with the invention is schematically illustrated in FIG. 1 and can be used for all anatomic sounds or sound signals independently of how they arose.

The first step in the signal processing is the detection of the sound signals. These are converted into electrically measurable values.

Sensors are generally used for such tasks. A sensor is a component which records a mechanical parameter and converts it after appropriate transformation into an electrical signal. This electrical parameter can be both the voltage and also the current or indeed the capacity. The sensor is however an analog component which signifies that it transmits time continuous signals which can have all desired values. For the signal analysis these must however first be digitized. This is brought about with an analog to digital converter ADW. However, during the conversion, the signal spectrum must be restricted with the aid of a low pass filter so that the Nyquist sampling condition remains satisfied.

One can also imagine under an ADW a sampler which samples or reads the analog signal in fixed time intervals and subsequently converts the analog value into a digital value by a quantizer. The precondition for this process is given by the Nyquist sampling condition which requires a minimum sample Rate Ts of twice the bandwidth W of the signal.

$$T_s \leq \frac{1}{2W}.$$

It should be furthermore pointed out that one can accommodate a plurality of sensors at different locations during the investigation.

After the preparation of the digital signal the actual signal analysis can be started.

For this a plurality of possibilities is available which, depending on the circumstances, can lead to the desired result. It should be emphasized that these tools are very different with regard to the complexity and the time required for the computation. When selecting the correct method a compromise must accordingly be found.

At this point two methods of signal analysis should be presented which are frequently used in practice.

The first method, which is simultaneously the simpler method consists in carrying out a fast Fourier transform (FFT) and subsequently comparing the frequency spectrum which is obtained in this way with other reference spectra (see FIG. 2).

Thereafter the signal which was originally set forth in the time zone is transformed in accordance with the equations into the frequency range. For this reason the method is also termed spectral analysis.

The advantage of this method lies in the fact that the intensity of all spectra or frequencies of a time interval can be observed very quickly and simply.

The Fourier analysis (FFT) is frequently used in the field of electrical communication technology and is concerned with a mathematic method for the analysis of complex wave forms or signals into a sequence of simple harmonic functions the frequencies of each are each an integral multiple of the basic frequency. The following applies:

$$Fn(f) = \int_{-\alpha}^{+\alpha} f(t) e^{-iwt} \cdot dt,$$

In the equation given above f(t) is the sound signal which is recorded as a function of the time (t). w signifies the basic frequency and Fn(f) signifies the Fourier transformation, i.e., the result of the Fourier analysis in the form of a sequence of the basic wave of the sound signal and its harmonics, with the respective amplitudes and phase shifts. α corresponds to infinity and the other symbols have the usual meaning.

If the information which is sought is embodied in the spectral distribution of the signal then one can best read out this information with FFT. The example of an osteoporotic bone is such a case. One can, by detailing the spectrum of the signals, rapidly determine whether this is a muffled sound or not.

The second method is the method of the neural networks which is very powerful and very informative and has many different variations. One should adopt this method for the investigation of the more complex patterns in the signal and for the recognition of incomprehensible patterns in the time zone.

Neural networks are logical circuits which can be compared with the functionality of our brain. As is the case with the brain they are capable of learning and can first be used after a learning phase. This has a role to play for the selection of the suitable learning patterns.

For the evaluation of the analysis one requires a reference with which one can compare the appropriate signal and then make a decision. This type of reference can be very different from case to case. It must however correspond with the method analysis.

Figure 2:
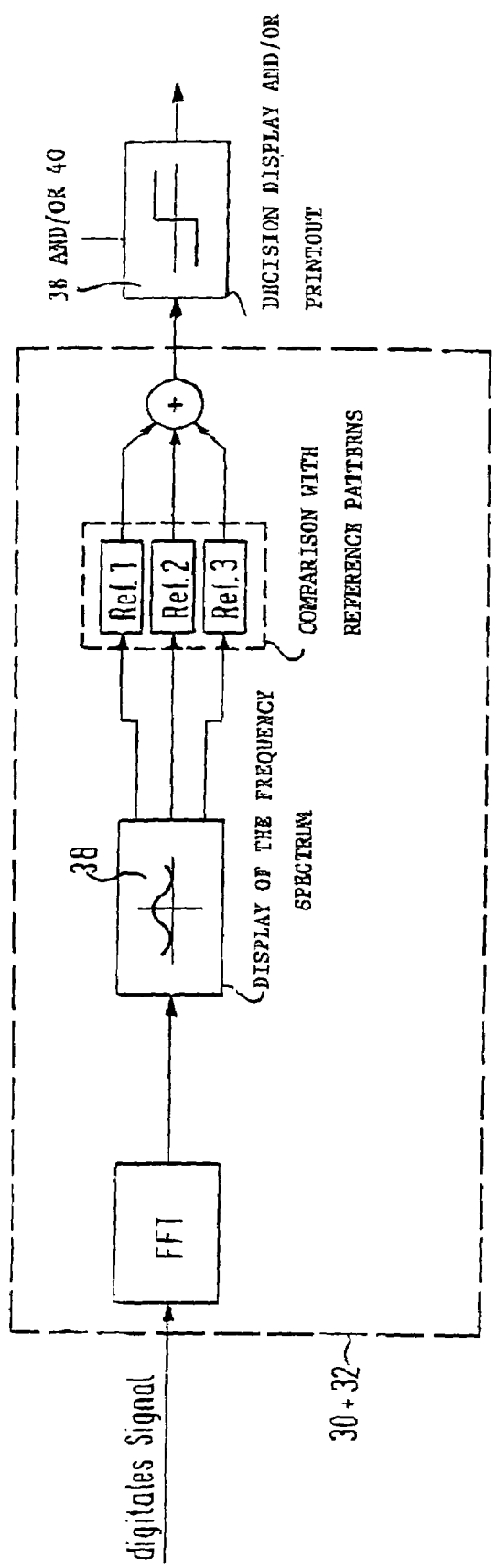

Now that two possibilities for the signal analysis have been presented, a practical example should be set out with reference to the FIGS. 1 to 3 and with reference to the determination of osteoporosis which represents a relatively simple and practical application, as is shown in FIG. 1. The sound signal to be investigated is caused by an external action 10 on a bone 12, for example on the tibia or on the head of the tibia by the blow of a doctors hammer. Through this, the bone 12 starts vibrating and transmits a sound signal 14. This sound signal 14 is picked up by a microphone 16 and is passed on as an electrical signal to a low pass filter 20. After the low pass filter the signal runs into an analog to digital converter 22 consisting of a sampler 24 and a quantizer 26. The output signal of the analog to digital converter 22 is a digital signal which is supplied to a device 30 which carries out an FFT analysis which provides particulars of the frequency spectrum of the sound signal 14, i.e. the base frequency which is present, its harmonics and the respective amplitudes.

The microphone itself is a type of a sensor. Other sensors, for example piezosensors can be considered and a plurality of sensors for example 16 and 16' can be used. When other sensors such as 16, 16' are used their respective digitized signals can be fed with appropriate identification into the input channel 28 of the device 30 which carries out the Fourier transformation. For some investigations it can also be advantageous to evaluate the signals of a plurality of sensors in order to make special diagnoses, for example at a knee joint. The identification makes it possible for the subsequent device 30 to respectively associate the signals of the various sensors with the latter.

The low pass filter restricts the bandwidth to a desired range, for example from 0 to 10 kHz.

The device 30 is moreover laid out in order to compare the frequency spectrum of the digital signal with a reference pattern or with a plurality of reference patterns which are stored in a memory 32 termed a "library". These reference patterns in the library 32 are based on earlier measurements, for example from the same patient, or from a patient of the same sex, same age, same weight or same body type. They can alternatively consist of reference patterns which are formed from measured values which originate from a group of patients who are comparable to the respective patient, for example with the criteria of same sex, same age, same weight or same body type, with such reference patterns also being subdivided into different classes depending on the degree of the osteoporosis.

In order to carry out the comparison it is advantageous to compress the data, for which purpose one of the known data compression processes can be used. The carrying out of the comparison is schematically illustrated in FIG. 2. As a result of the comparison that is carried out one succeeds in determining whether the respective patient has osteoporosis and if so the degree of the illness.

The devices 20, 22, 24, 26, 28, 30 and 32 an be formed by a computer 34 as is indicated by the box in FIG. 1 with the same reference numeral. The computer can for example have available a keyboard 36 for the inputting of patient data, time details and commands, a screen 38 for showing the result of the measurements and the reference pattern which is considered, or the reference patterns which have been considered, and also a printer 40 for printing out the results.

In a practical version of the invention the sound signal can be passed on to the sound card of the computer which directly takes care of the filtering and digitalisation tasks and subsequently the analysis.

The basic idea of this acoustic investigation of the osteoporosis is based on the concept that the human bone, just as any other object, should sound different depending on the enclosed content. That is to say the more porous the bone is the more muffled it should sound when tapped. This characteristic can be very well observed by way of a spectral analysis. This corresponds to an accumulation of the low frequency components of the spectrum. After the FFT of the signal the shift of the spectrum in the low frequency range can be made visible.

As a result of the investigations on previously and precisely diagnosed patients and healthy patients some examples will now be given which show that the above named method operates in a problem-free manner with osteoporosis.

Thereafter the plausibility of the method which has been presented will be shown with reference to healthy probands and osteoporosis patients pre-diagnosed by means of, for example, osteodensitometry.

In addition, the theoretical possibilities of the diagnostic signal analysis will be shown with respect to the large joints.

Furthermore, references will be made to the theoretical possibilities of the diagnosis of soft tissue diseases.

FIG. 3A shows the result of the measurement at a healthy bone of a 42 year old man.

The x-axis specifies the frequency in Hz whereas the y-axis delivers a potential value in V. The height of the base line, i.e. the start at the y-axis in V depends on the sound strength and does not appear to be dependent on the patient, it is thus probably unimportant for the evaluation. However the amplitudes at the individual frequencies, i.e. the relative amplitudes of the frequency peaks, compared to one another, deliver important information.

In order to receive a clean signal the tibia is tapped several times. The signal was evaluated at the tenth time. As described above, the impulses were made with the doctors hammer on the ventral tibia approximately 5 cm below the knee joint gap, with the measurement being made at the tibia head.

FIG. 3B shows the bone of an osteoporotic male patient (44 years). The measurement was recorded as described above in connection with FIG. 3A but here for the first tap. Although the patient is of a similar age to the healthy patient on which the measurement of FIG. 3A was carried out there are visible shifts of the spectrum into the low frequency ranges. The difference can be seen clearly: the 44 year old patient was previously diagnosed by means of osteodensitometry. The standard deviation amounted to 1.75.

One can classify the osteoporosis as manifest.

Figure 3C:
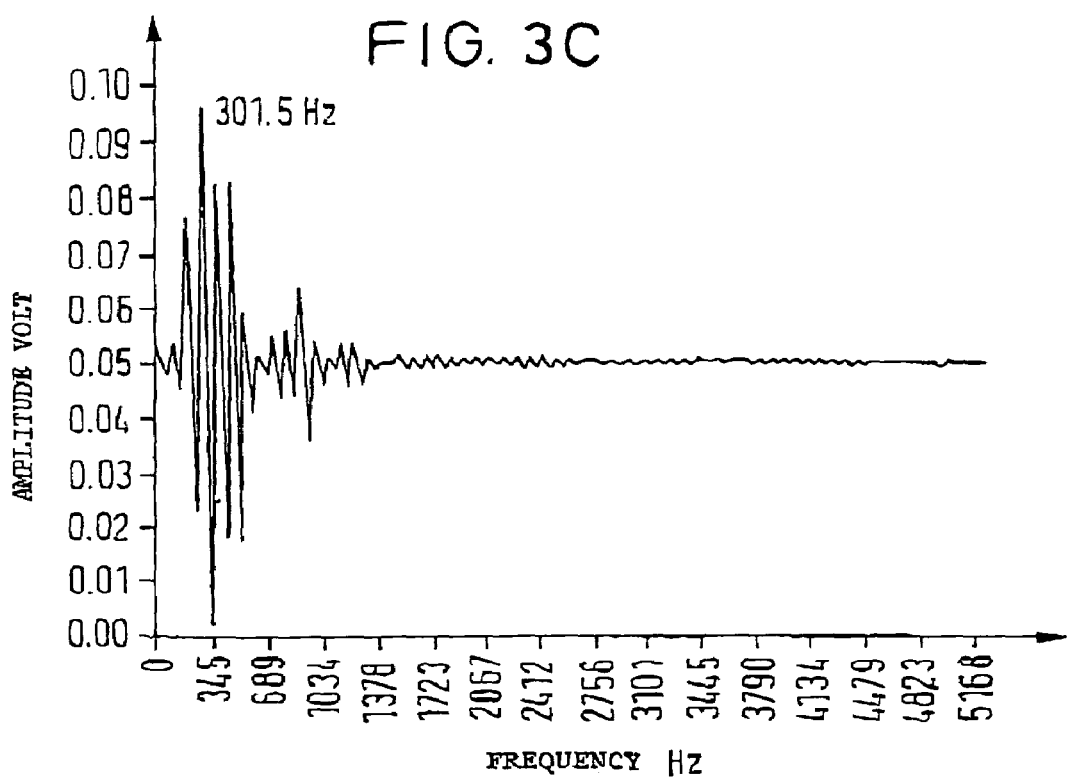

FIG. 3C shows the bone of a 64 year old patient with an average degree of osteoporosis.

According to the finding by densitometry the bone density reduction amounts to 10–15 percent. In this case the knocking sound was evaluated at the fourth time.

Figure 3D:
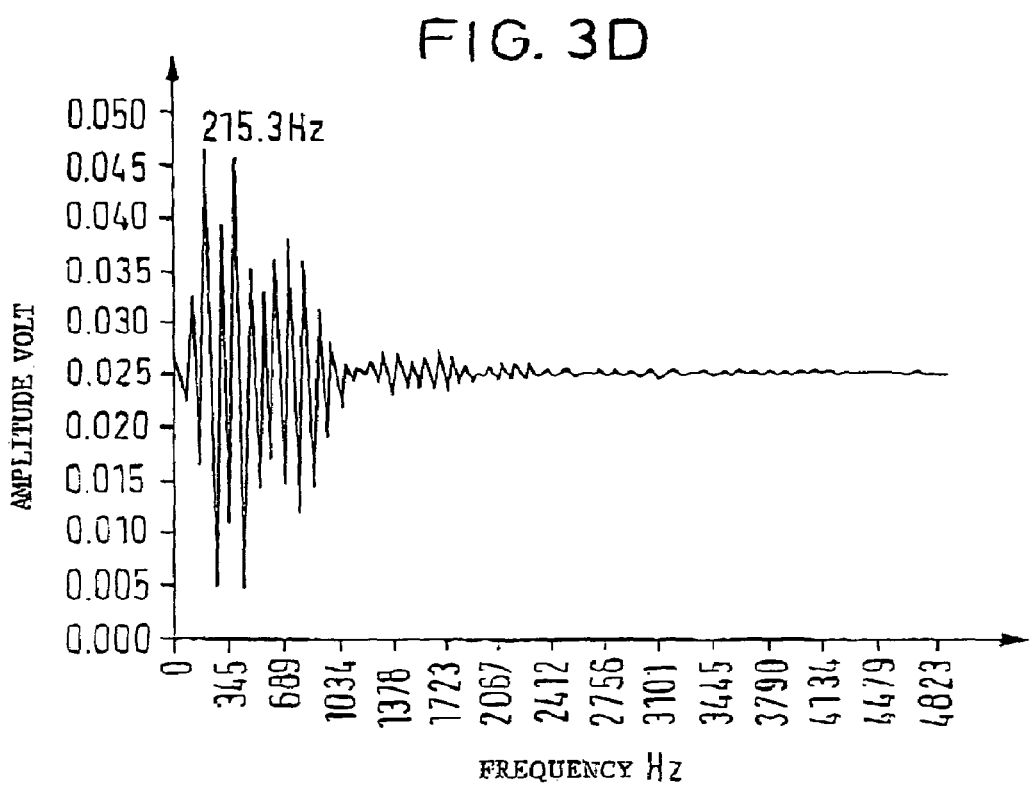

FIG. 3D shows the measurement of a 72 year old patient with serious osteoporosis and having undergone several fractures, including compression fractures of the spine. In this case the sound was measured at the second time. The visible result is very impressive.

Figure 3E:
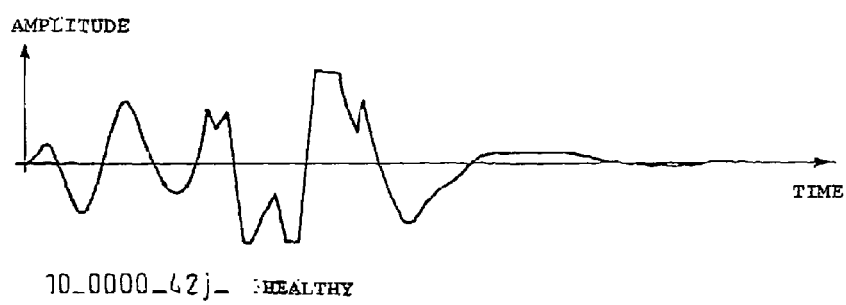
Figure 3F:
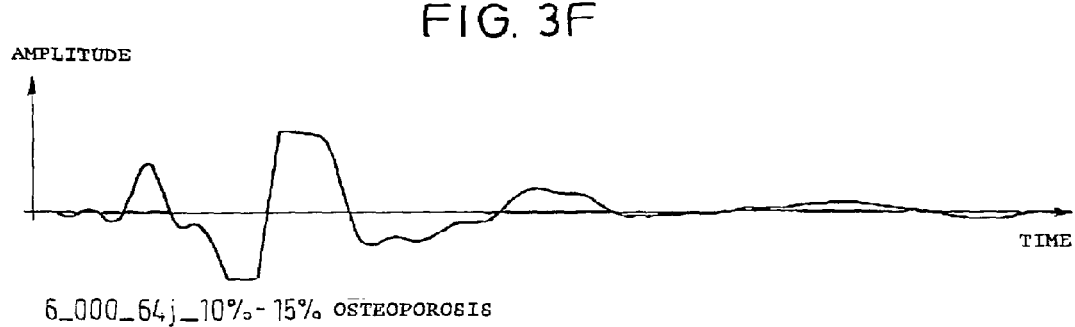

FIGS. 3E and 3F show the difference of the amplitude between a healthy bone (patient in FIG. 3A) and an osteoporotic bone (patient in FIG. 3C) even before the computer evaluation.

Notable is the width of the amplitude for a person with osteoporosis. For a healthy person the amplitude appears to be reduced in time (if anything) and peak-like.

The above named examples were investigated or recorded by means of a normal microphone. It is to be assumed that when using the special sensors the results would appear even more impressive and more precise. That is to say the method presented functions in principle.

Further investigations of joints and bones have shown that in fact many noises can be associated with a number of specific illnesses.

An important part of the work is the generation of reliable references, since the reliability of the decisions that are made depends strongly on the correct choice of references.

It is however already certain, even without references, that a distinction can be made between healthy and osteoporotic bones. Simply for this reason this method should find broad acceptance. By reliably excluding osteoporosis unnecessary X-ray investigations and diverse densitometric investigations can be avoided.

The savings in expenses of the patient and of the health insurer can be enormous.

The above named concept of the bone density measurement (osteodensitometry by means of measurement of the longitudinal wave sound) will also be able to be transferred to software without problem in the future. This relates also to the development of special programs with investigation of the joints and soft tissues as named above. The future of software manufacture will presumably enable in a short period of time osteoporosis investigation in every practice which is equipped with a computer. Merely the simple confirmation or preclusion of osteoporosis without significant cost and work is to be regarded as an enormous step for the daily activity of the doctor in the practice. An internet transmission can also be involved in the investigation. For example a doctor's practice can call up reference patterns from other sources (doctor's practices and the like) via the internet. As an alternative the computer 34 can send the result of an actual measurement (with or without prior evaluation) via the internet to an evaluation center or computer center where the evaluation is carried out. The results of the evaluation can then be supplied online to the computer 34 to be displayed and/or to be printed out. In this manner the measurements of a large member of practices are available to form high quality reference patterns, above all when they are linked with the result of further measurements, such as osteodensitometry measurements on the same patient.

It is also entirely conceivable for the reference patterns to be made available to individual doctors practices and other institutions stored on a storage medium, for example on a CD.

The attached reference list contains details of literature sources which deliver information concerning signal analysis in general and which can be used for assistance if required. Although the previous description is concerned with measurements on humans, the method of the invention and the apparatus of the invention can also be used in connection with animals, above all with race horses, for diagnoses, for example with respect to their suitability for racing and the danger of fracture.

FIG. 4 shows a schematic representation of the right hand knee joint of a human with FIG. 4A showing the illustration from the front with the femur bone 100, the tibia 102 with the tibia head 104 and the fibula 106. The reference numerals 108 and 110 point to the outer meniscus and the inner meniscus respectively.

FIG. 4B shows the same representation seen from the outer side of the knee and additionally shows the knee cap or patella 112.

FIG. 4C likewise shows the knee cap 112 here in a representation corresponding to the longitudinal axis of the femur bone 100, with the knee being shown axially in the bent position and with the femur sliding roll 107 being visible. This representation is a representation of a physiologically "ideal" knee joint, i.e. a joint in a good condition. The double arrow 114 indicates the movements which occur during bending and stretching of the knee joints.

In contrast FIG. 4D shows a similar joint in which the condition of a medial osteoarthrosis is present, i.e. a wear of the inner joint gap which is shown at 116. This arthrosis 116 makes itself notable in the noise spectrum when bending at the knee joint in accordance with the arrow 114, which is also evident in the schematic illustration of FIG. 4D.

An apparatus for recording the noises which arise on bending at the knee joint is shown in FIG. 5. This is an elastic stocking 120 which is drawn over the knee joint and which is equipped in this example with three microphones 122 which are coupled via lines 124 to a computer such as 34. Instead of using three microphones one can also operate with a single microphone and other sensors which pickup acoustic signals can also be used. It is also not necessary to connect the microphone to the computer via signal lines 124 but rather a wireless transmission could be selected. For this purpose a transmitter unit with appropriate batteries is incorporated into the stocking so that the signal transmission to the computer takes place by means of infrared signals or using another wireless transmission, with it naturally being necessary for a corresponding receiving unit to be associated with the computer 34. In this example the knee joint is either (actively) moved by the patient himself or which is moved manually by a doctor or an assistant, i.e., passively.

It is however, best of all when the microphones are installed into an auxiliary device or orthosis which can be secured to the knee joint independently of the anatomic circumstances of the joint. The stocking 120 can form a part of this auxiliary device or the microphones can be mounted onto the auxiliary device in another way or means. The sense of the auxiliary device is to ensure that the sound pickup always takes place with a like movement of the knee joint so that the recorded sound signals are reproducible; whereby, on the one hand, a comparison of the recorded signals of the respective patient or program with reference values on which were recorded under the same conditions is made possible, and, on the other hand, the comparison is also possible with other recordings for the same patient or proband, i.e. a comparison between recordings made at different times.

One form of the auxiliary device would be a splint or brace which follows or forces the natural movement of the joint. For example, a splint can be used for the knee joint such as is used in hospitals for the post-operative movement of the knee joint of a patient who has, for example, suffered ripping of the cruciate ligaments which was cured surgically. With an apparatus of this kind the upper leg of the patient lies on a first splint whereas his lower leg lies on a second splint which is connected to the first splint via a polycentric joint and is driven relative to the first splint by a motor in order to force movements about the polycentric joint and to carry out corresponding movements of the knee joint of the patient. This splint can be operated for the purpose of the invention and also without any motor when the second splint is (actively) moved by the patient himself or (passively) moved by an assistant about the polycentric joint. An apparatus of this kind could be termed a CAPM orthosis (Continuous Active/Passive Motion orthosis).

Figure 6A:
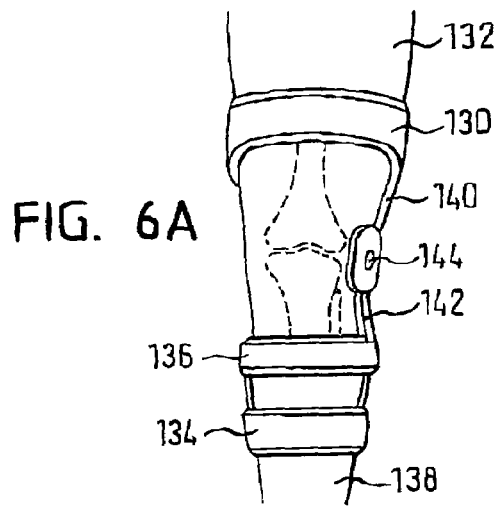
Figure 6B:
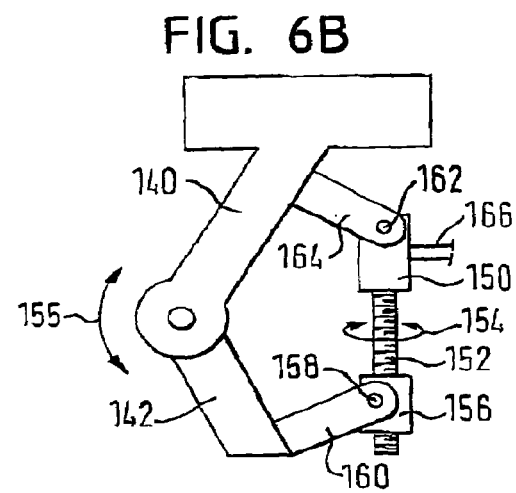

Another possible design of the auxiliary device resembles a knee orthosis known per se such as for example shown in FIG. 6A. This is a knee orthosis such as is available from the company Medi Bayreuth in Germany and is sold under the designation "Monarch GA". This orthosis consists of a fixing band 130 which is secured around the upper leg 132 of the proband, for example with the aid of a hook and loop fastener and also of two lower bandages 134 and 136 which are secured to the lower limb 138 and can likewise be provided, as an example, with a hoop and loop fastener. Arms 140 and 142 which are in principle rigid and which are secured to one another at a joint 144 extend from the upper fastening band 130, or from the upper fastening bands 130 if two are provided, which is also possible and from the lower two bands 134 and 136. The joint executes a polycentric movement in accordance with the movement of the human knee joint and is aligned with the knee joint of the patient or of the proband. This arrangement of the two arms 140 and 142 can also be repeated at the left hand side of the lower leg in FIG. 6A, which is not shown here. In order to force passive movements of the knee joint a motor 150 can be secured to this orthosis as shown in FIG. 6B. This motor 150 drives a threaded spindle 152 in two alternative directions of rotation which are shown by the double arrow 145. In this connection the threaded spindle extends, as shown in FIG. 6B, through a nut 156, which is pivotally secured about the axis 158 to an arm 160 which is rigidly connected to the arm 142.

The motor 150 itself is pivotally hinged about the axis 162 to a further arm 164 which is firmly connected to the arm 140. The motor can be controlled from the computer 34 via the lines 166 in order to turn the spindle 152 alternatively in the one or other arrow direction 154. In this way a polycentric movement of the knee joint is forced in accordance with the design of the joint 144 and this movement is also precisely predeterminable via a computer 34 with respect to its amplitude, speed and frequency, so that the same movement is ensured for all probands or patients. For patients with knee problems a different amplitude of the movement of the knee joint can be preset optionally via the computer 34 or a special motor control so that they do not suffer unnecessary pain or indeed damage. The speed of the movements and the repetition frequency can also be selected correspondingly differently if required. The motor 150, the spindle 152 and also the arms 160, 164 which carry the spindle and the associated parts 156, 158, 162 are preferably so designed that they are easily removable. For example they can be secured to the orthosis by clipping them in place so that they can be removed "with one click". In this manner the auxiliary device can easily be converted into a normal orthosis.

FIG. 7A now shows in a three-dimensional representation the result of a recording of knee joint noises in a proband with a knee joint in good condition in accordance with FIGS. 4A to 4C.

This recording was made using a program for acoustic signal analysis which is commercially available as a tool for the most diverse acoustic signal analyses. This is the Wave Lab program which is obtainable from Herrn Steinberg or from Miro Computer Products AG, Cham, Germany.

The investigation is carried out with a special microphone connected to the computer. The sounds are recorded at specific joint positions. For the precise investigation it is, however, as already mentioned, necessary to use a special splint device or orthosis.

The evaluation now takes place with a standard program for the frequency analysis, for example Wave Lab Steinberg (see above). Both mathematical data is stored, such as sound level, loudness, peak, and also a schematic representation is used. A totally inconspicuous joint without pathological noises of the soft tissues, of the cartilage and others is shown schematically in three dimensions in the form of a frequency analysis.

Three parameters are shown: frequency in Hertz, amplitude and the time from 0 to the end of the investigation (here after 8 seconds). The joint is moved several times, on average five times. After fast Fourier analysis the computer processes the acoustic joint situation. For an inconspicuous joint, as in this example, the levels marked in color are very regular, as schematically illustrated. The amplitude of the frequencies between 20 Hz to about 30 Hz is the highest (the first three-dimensional structure on the left, i.e. with the signal color brown). The next structure from about 40 Hz to about 50 Hz is on average smaller by half, i.e. with the signal color red. Then follows again a structure which is smaller by one third at about 50 Hz to about 80 Hz, i.e. at the signal color orange. The next levels from 150 Hz onwards are extremely low and are only indicated i.e. at the signal color yellow. At the frequency of about 3600 Hz there is again a small rise, which is indicated with the signal color blue.

The time plot on the levels is symmetrical, no differences from about 0 to 1 second and from about 0 to about 8 seconds (depending on the length of the investigation).

The pathological joint shows itself to be different, independently of a specific diagnosis. An example is set out in FIG. 8A for a knee joint which has a medial osteoarthrosis. There is a very precise correlation between functional diagnosis and the schematic representation and the mathematical data. For example, with a medial osteoarthrosis significantly lower levels at 20 Hz to 40 Hz can be seen as in FIG. 8A, in contrast individual partly high and irregular peaks 171 are present at 115 Hz. The determining factor is the frequency and the height of the levels between 200 Hz to about 1000 Hz (here marked yellow). The seriousness of the arthrosis, i.e. of the frictional processes of the damaged cartilage/bone structures is shown in this region. Of less significance are, in this case, the structures at 3500 Hz, 8000 Hz and about 18000 Hz. With relief of the joint parts (effected either manually and with the already described rail) or with the known orthosis (Monarch GA) these parameters change. With this program the levels (amplitudes) at the frequencies between 200 Hz to 650 Hz are significantly smaller. The amplitudes of the lower frequencies are in contrast higher. From this diagnostic conclusions can be drawn (as already described).

The computer shows a quite different picture and quite different but specific mathematical parameters for soft tissue diseases. For example for tendovaginitis stenosans of the thumb (jerking thumbs) the levels at 20 Hz or 40 Hz are extremely low. The yellow levels are also not present. The noise is very loud and has quite different characteristics from the joint noise.

FIG. 7B shows how this three-dimensional frequency analysis can be reproduced, for example in form of a bar diagram. With a computer representation one can for example, call up the histogram or the three-dimensional representation as in FIG. 7A (or both at the same time) and these representations can also be shown in color so that the different colors are associated with the respective frequency ranges, as is indicated in FIGS. 7A and 8A.

Thus the present invention enables, by evaluation of the noises which originate from a joint an unambiguous diagnosis of the condition of the joint and it is to be expected that the different signal evaluations will turn out so differently that one can diagnose all important medical problems in the region of the knee joint, also in connection with the soft tissues, such as the meniscuses, by different frequency spectra of the recorded signals. Not only the frequency subdivision delivers useful information concerning the respectively present disease or change of condition of the knee. It is for example evident from FIG. 8A that the frequencies in the range of about 150 to about 1000 Hz again have discrete peaks which are also characteristic for a knee with arthrosis in accordance with FIG. 4D.

Investigations in the practice of the applicant have shown that a justified hope really does exist of being able to make a diagnosis for all relevant knee joint diseases and indeed in a way and means which is not in principle painful for the patient and which can in any event under some circumstances prevent some unnecessary medical operations. The same also applies for all other joints of the human where movements of bones or soft tissues occur.

The invention can however not only be used for diagnoses as described in connection with the FIGS. 4 to 8 but rather it can also be useful for therapeutic treatment of the respective joint. In order to give an example for this reference will once again be made to the representation of FIG. 6A.

It has already been brought out above that this is an orthosis of the company Medi from Bayreuth. With an orthosis of this kind air chambers are built into the bands 130, 136, 124 and in the region of the joint 144 which can be pumped up by means of an air pump. It is possible in this manner or with a screw arranged in the region of the joint 144 to exert a lateral pressure onto the knee joint so that, for example, with wear effects of the joint in the region of an inner meniscus 108, the knee joint gap at this position can be opened slightly and for this the knee joint gap in the region of the outer meniscus is if anything loaded more. Through this relief of this damage point of the knee joint, by opening of the knee joint gap, a relief arises here which is reflected in the noise signal. Thus the doctor, or an orthopaedic technician, can move the knee joint, optionally with the aid of the apparatus of FIG. 6B, but also without using the motor and can consider the frequency analysis until this shows that noises no longer occur in the region of the inner meniscus 108. As soon as this is achieved he knows that an adequate relief of the knee joint has been achieved and the patient can move with the apparatus in the intended way and means while the effected joint portion recovers or is brought into a better condition by special medication or treatments. After the setting of the joint gap the motor 150 and the associated parts can be removed from the orthosis, as previously indicated. During the therapy the patient walks around, i.e. carries out his daily work with the attached orthosis, but without the motor 150.

When it is stated that the joint is moved without using the motor 150 then this is to be understood in the sense that the patient himself bends his knee, for example in that he carries out easy knee bends or walks, this would then be active movements of the knee joint. Alternatively the patient can allow his knee joint to be moved manually by another person while sitting down or reclining, this would then be passive movements.

Figure 9A:
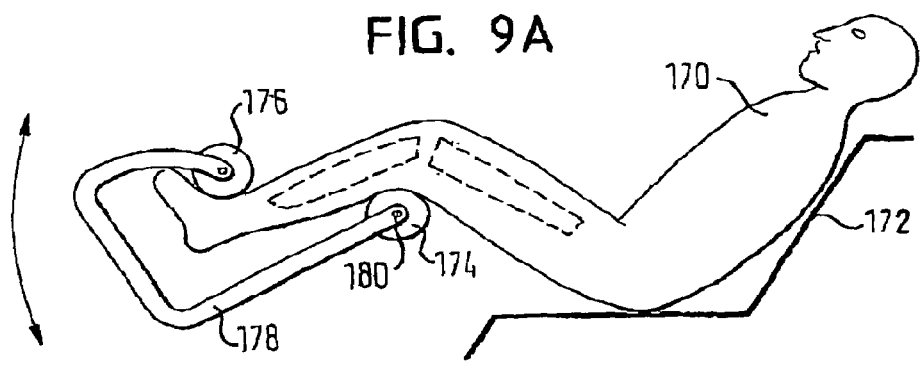
Figure 9B:
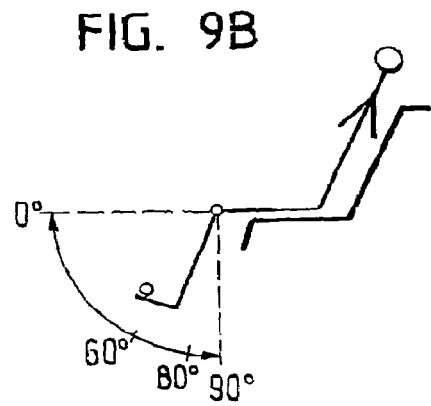

When the therapy is ended, i.e. an initial improvement of the condition of a knee joint has arisen, the phase of the rehabilitation then begins. Here the patient is either in the care of a physiotherapist or can himself go to a fitness studio and use the exercise machines which can be used there which are intended for a strengthening of the knee joint and the muscles associated with it. An apparatus of this kind is schematically shown in FIG. 9. Here the patient 170 sits on a seat part 172 of an apparatus with a fixedly arranged but rotatable roller 174 which is arranged in the back of the knee of the patient and supports his knee. In this the feet of the patient engage beneath a cylindrical bar-like part 176 which is rotatable via a chassis or a frame 178 about the axis 180 of the roller 714. The patient has to attempt to lift the part 176 with his foot, so that the chassis 178 pivots about the axis of rotation 180; in this arrangement a pivotal movement in the range between 0° and 90° would be usual, as is evident from FIG. 9B. Such apparatus are designed so that the resistance to this rotary movement can be set. One can now imagine that the patient again pulls on the stocking of FIG. 5 and that the acoustic signals are again recorded during this movement on the exercise machine. For example, it will then turn out, for example as a result of arthrosis in the region of the knee, that an unpleasant friction occurs in the knee joint in the angular range from, for example, 60° to 80°, so that precisely in this region of the movement a resistance which originates from the exercise machine should be kept as small as possible. In contrast, in the range of movement between 90° and 80° and between 60° and 0° no poor points of the knee joint are loaded, so that one can operate here with an increased resistance so that the desired condition is achieved. In other words the resistance characteristic of the exercise machine is specifically set in accordance with the respective patient. The rehabilitation of the knee joint by building up the muscles then progresses as desired without the damaged portion of the knee joint, which has to be rehabilitated, being loaded. The exercise machines which are laid out in this way are not only to be used for rehabilitation but can also be used in leisure time for fitness training.

Here the example has also been given with reference to a knee joint. It is, however, self-evident that any other type of exercise machine which is intended to train special muscle regions can be designed accordingly in order to rehabilitate or to train the respective associated joint of the patient.

Instead of installing the sensors in a knee stocking they could also eventually be incorporated into the exercise machine itself and indeed the exercise machine could also be so designed that it automatically adjusts itself while evaluating the recorded sound of signals, so that damaged joint positions are protected and can be more quickly rehabilitated. Once a specific setting of the exercise machine has been found for a specific patient then the setting can be stored specifically for the patient and can be retained for future exercises on the machine, so that it is not necessary for each renewed use of the exercise machine to determine the settings anew, or for the patient to again pull on a knee stocking with microphone.

The invention however goes even further. One can imagine that the invention is used for the setting of ski boots or other devices used in the most diverse types of sport. This will be explained with reference to new ski boots.

It is known that good skiers, such as for example Hermann Maier, can move far into the forward knee position, i.e. can bend the knee to an extreme degree without suffering pain or deterioration of the joint to a pronounced degree. In contrast there are other skiers who are older or who have a weaker musculature or have already damaged knees who could not practice such an extreme forward knee position as Hermann Maier. It will be good if in this case this ski boot could be designed so that, in a specific forward knee region, it either blocks or exerts a resistance against a further forwardly disposed position, i.e. further knee bending. For example this could take place by special spring arrangements in the boot or by swapping shin pads which are differently supported at the front part of the boot and thus restrict the forward knee position of the skier. One can now imagine that the skier who wishes to procure a new pair of boots goes into a shop, pulls on a stocking in accordance with FIG. 5 and carries out knee bends, i.e. active movements under load (for example with weights on the shoulders). Passive movements would also enter into question, i.e. the apparatus of FIGS. 6A and 6B could also be used here. If now the acoustic signal analysis shows that the respective skier can easily achieve a forward knee position up to 30° but that a further going forward knee position beyond this angle leads to an undesired loading of the knee joint—determined by the changing knee sounds—then the respective sport shop knows that the boots suitable for him must be set or selected such that they block a forward knee position of 30° or make a movement beyond 30° substantially more difficult. This prevents the skier skiing in a forward knee position which is damaging for him.

In order to realize this it is naturally necessary, which is also sensible with the embodiments described here, for the joint noises to be evaluated in an angle specific manner in accordance with the degree of bending of the joint, which also requires a device to be provided which measures the degree of bending.

If the signals are recorded using an orthosis in accordance with FIG. 6B then an angular measuring device can for example be incorporated in the joint 144, or the control signals for the motor 150, can be used for this purpose. For example, the motor could be turned in one direction until the spindle 152 has been almost screwed out of the nut 156 so that the joint is located in its extended position. When the stop is achieved here this is assumed to be 0° of bending. If the motor 150 is for example designed as a stepping motor then a precise determination of the respective bending angle of the apparatus for each movement on the stepping motor and of the spindle can be found from the particulars of the pitch of the thread of the threaded spindle 152 and the geometry of the orthosis.

Figure 10:
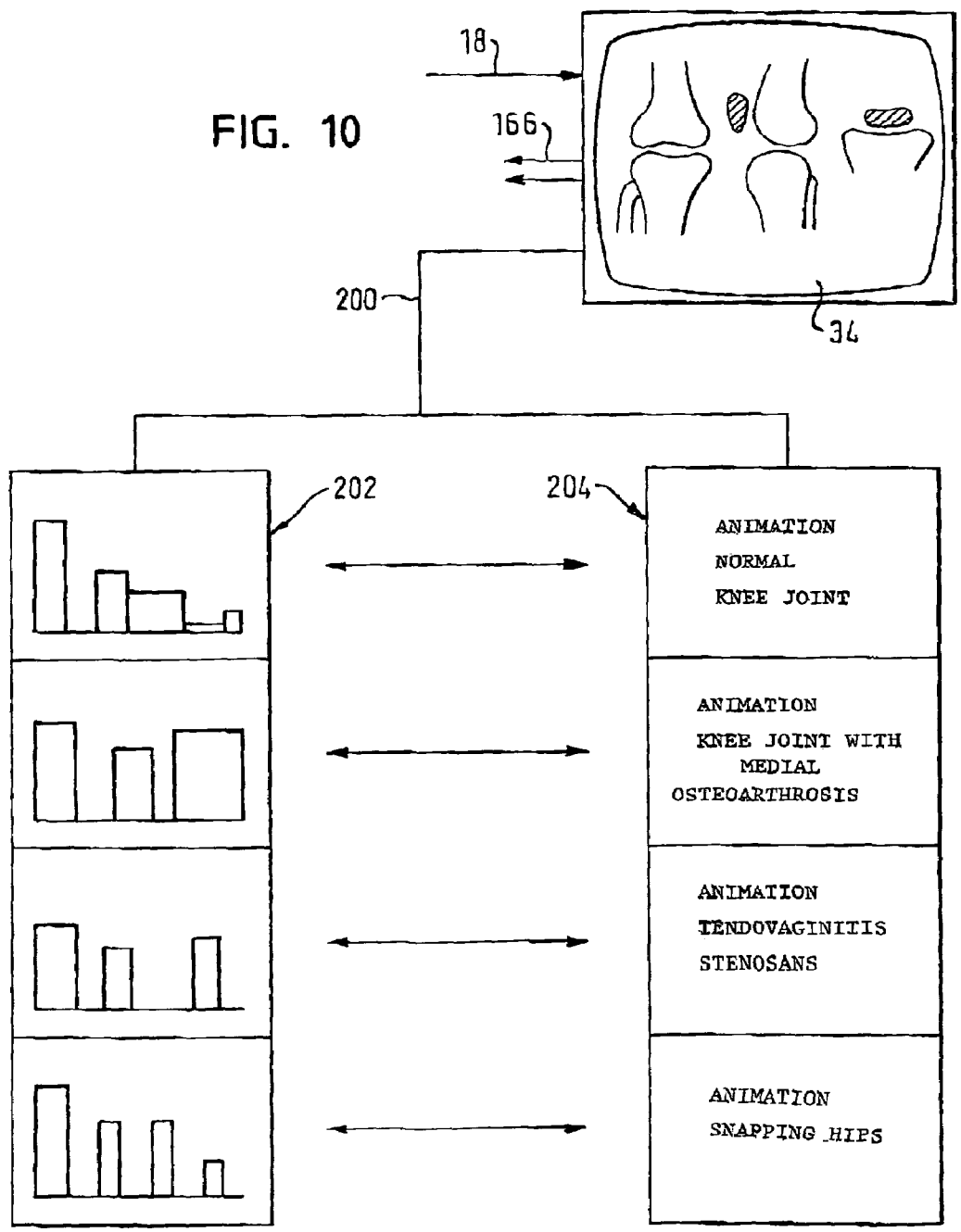

A special feature of the present invention lies in the fact that an animation is possible which facilitates the diagnosis of the respectively present problem and is also easily comprehended by the patient or proband. With reference to the knee joint one can now imagine that the pictures which are shown in FIGS. 4A to 4C appear schematically in the screen of the computer 34, as shown in FIG. 10, and on the movement of the knee joint the corresponding movement of the joint parts is shown on the screen by an appropriate animation. Here the angle signals which are discussed above can be useful for the purpose of the animation. In any event the signal evaluation can be used in order to indicate on the screen animation the regions where problem positions are to be found as a result of the signal evaluation. For example, the corresponding positions could be emphasized on the screen by a flushing representation or by a special coloring, so that the doctor can for example say to a patient "Look at that, your inner meniscus is damaged" or "You are suffering from arthrosis". This emphasizing of the damaged positions can either take place by a static representation of the joint images according to FIGS. 4A to 4C or with a simultaneous movement of the joint members or, if the problem only occurs in a specific angular range in a representation which corresponds to this angular range, for example with an angular bending of the knee of 30°, which could above all be indicated in accordance with the illustration of FIG. 4B. One possibility of realizing such representation is shown schematically in FIG. 10. Here we see the above discussed computer 34 and it is illustrated schematically that the computer communicates via a data line 200 with two memory areas 202 and 204.

These memory areas 202 and 204 can be present in the computer itself or they can for example be realized in the external memories, for example remote memories. The data line 200 could for example also be understood as an internet connection so that the computer 34 stands in the doctor's practice, whereas the memory regions which can be accessed by the computer 34 stand at a remote location.

Figure 8B:
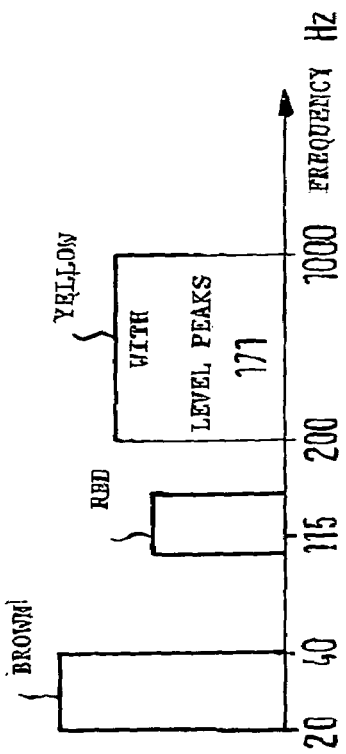
Figure 8A:
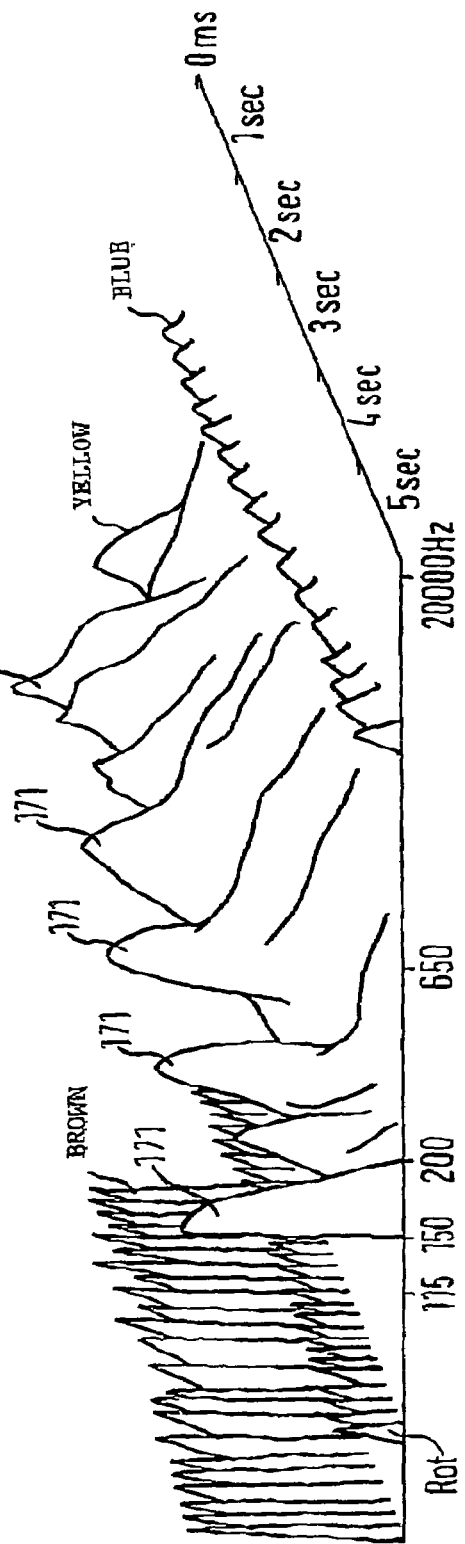

In the memory 202 there are then, for example, stored a series of histograms corresponding to FIGS. 7B and 8B whereas in the region 204 corresponding representations of the knee are contained illustrating the respective problem. i.e. the computer 34 carries out a spectral analysis as a result of the respective recordings by the doctor, which are supplied to the computer via the line 18, and accesses the correspondingly stored reference histograms or patterns from the region 202 and the matching pictures from the memory 204 and shows them on the screen. When the joint shown on the screen is moved in the context of the animation in accordance with the movement of the joint being investigated then this movement in the screen can take place substantially more slowly so that the problem areas can be more easily recognized by the viewer of the screen. Although only four memory regions for frequency analysis and animation possibilities (202A, 202B, 202C and 202D and 204A, 204B, 204C and 204D) are shown in FIG. 10, in practice a large number of different frequency analyses and animation possibilities or diagnoses is stored. FIG. 10 is to be understood purely by way of example and applies not only for knee joints but rather for all other joints which come into question.

Summarizing it is emphasized that a computer program with a specific representation of the joint that is investigated will be relatively simple to produce. One can schematically represent every joint analogously to the above described scheme. Problem zones such as, for example, frictional processes, trapping of soft tissues, trapping of meniscuses etc. could be shown schematically. In this way a particular person can observe his joint during the movement. In similar manner one can show soft tissues such as the point of trapping in the cause of the tendon. This would be a very important aspect in rehabilitation, performance sports etc. The bio feedback roll should also not be forgotten. For example, with pathological pressure of the patella on the upper limb sliding roll between, for example, 60° and 80° an exercise machine could be especially set (analogously to the Cybex 2-apparatus). In this way one could avoid the pathological friction processes in this range. A further example for the use of this method (data bank, corresponding apparatus, corresponding joint splint with sensors or microphones) would be the adaptation of the ski shoes with respect to the knee joint. A majority of skiers suffer retropatellar pain, such as for example chondropathic patella. The acoustic determination of the forward knee position of the shoe could take place depending on the pathological signals from the knee joint. It would be of great importance both for the performance skier and also for the recreational skier. With a physiological, non-damaged joint a very wide/soft forward knee position is naturally possible without restriction. With pathology a difficult forward knee position should be used in dependence on the acoustic signal. This is the only method where a picture yielding method comes about in orthopaedics from an acoustic signal. The advantage of this method is an active representation—for example bending and extension, which can be repeated as desired.

An animation (computer animation) of the joint model controlled by acoustic waves from the real joint is realized, with this animation being capable of being used both in investigations, in therapy, in rehabilitation and/or during training.

The possibility of diverse attachment of an auxiliary device to the whole or to part of the extremity should also be pointed out, with the auxiliary device being able to have one joint or several joints. Moreover, the possibility of adjustable and measurable movements (and force distribution) in all planes should be pointed out coupled to adjustable main movement; for example the possibility of additional distractions, compressions and rotations, for example of physiological end rotations also with knee extension, additional compression with fractures or after operations and utilization of the distraction relief or action on the whole joint, not just one sided pivoting opening or distraction, analogous to the methods of Ilisarow, for example with bone extension.

What is claimed is:

1. A method for determining the anatomic condition of components of the body of a human or of an animal having joints, comprising:

utilizing an auxiliary device selected from the group consisting of a brace, an orthosis, and an exercise machine to cause reproducible passive movements or reproducible active movements of at least one joint to produce a sound signal in a selected component of the body associated with said at least one joint;

recording said sound signal at a point adjacent to the selected component of the body;

evaluating said sound signal, by a spectral analysis of frequencies and amplitudes contained in said sound signal;

making a comparison of the outcome of said spectral analysis with a plurality of stored reference patterns for corresponding spectral analyses for the diagnosis of the anatomic condition; and indicating the result of a diagnosis as a screen display in the form of an animation in which the illustrated joint executes movements which correspond to those of said reproducible movements of said at least one joint, with these movements being indicated either synchronously or asynchronously to the actual movement of said at least one joint, said at least one joint being schematically illustrated on the screen display and the diagnosis being indicated visually by highlighting of damaged positions on said animation.

2. The method in accordance with claim 1, wherein the animation on the screen display is effected to be substantially slower than said passive or active movements of the joint, for the purpose of easier comprehension of the damage which is present.

3. The method in accordance with claim 1, wherein the auxiliary device is used for the therapeutic treatment of the joint and the setting of the auxiliary device is effected with reference to the sound signals that are recorded.

4. The method in accordance with claim 1, wherein the auxiliary device is designed for at least one of the rehabilitation of the joint, the training of the joint and the training of the muscles associated with the joint.

5. The method in accordance with claim 1, wherein said highlighting comprises at least one of colouring of, lighting up of, and flashing of said damaged positions.

6. The method in accordance with claim 1, wherein the result of the diagnosis is also printed out.

* * * * *